US012082901B2

(12) United States Patent
Mirbagheri et al.

(10) Patent No.: US 12,082,901 B2
(45) Date of Patent: Sep. 10, 2024

(54) CONTROLLING A LAPAROSCOPIC INSTRUMENT

(71) Applicants: Alireza Mirbagheri, Tehran (IR); Golchehr Amirkhani, Tehran (IR); Seiedmuhammad Yazdian, Tehran (IR); Farzam Farahmand, Tehran (IR); Saeed Sarkar, Tehran (IR)

(72) Inventors: Alireza Mirbagheri, Tehran (IR); Golchehr Amirkhani, Tehran (IR); Seiedmuhammad Yazdian, Tehran (IR); Farzam Farahmand, Tehran (IR); Saeed Sarkar, Tehran (IR)

(73) Assignee: SINA ROBOTICS AND MEDICAL INNOVATORS CO., LTD., Tehran (IR)

( * ) Notice: Subject to any disclaimer, the term of this patent is extended or adjusted under 35 U.S.C. 154(b) by 1174 days.

(21) Appl. No.: 16/832,439

(22) Filed: Mar. 27, 2020

(65) Prior Publication Data
US 2020/0222113 A1 Jul. 16, 2020

Related U.S. Application Data

(60) Provisional application No. 62/824,327, filed on Mar. 27, 2019.

(51) Int. Cl.
A61B 34/00 (2016.01)
A61B 18/00 (2006.01)
A61B 34/37 (2016.01)

(52) U.S. Cl.
CPC .... *A61B 34/77* (2016.02); *A61B 2018/00636* (2013.01); *A61B 2018/00916* (2013.01); *A61B 34/37* (2016.02); *A61B 34/75* (2016.02); *A61B 34/76* (2016.02)

(58) Field of Classification Search
CPC ......... A61B 34/37; A61B 34/75; A61B 17/29; A61B 18/1445; A61B 34/30; A61B 2090/067; A61B 34/71; A61B 34/77; A61B 17/282; A61B 2017/2926; A61B 17/28; A61B 17/2812; A61B 17/295; A61B 2017/2927; A61B 2017/2929; A61B 2017/293; A61B 2017/2931; A61B 2017/2932
USPC ........................................................ 606/205
See application file for complete search history.

(56) References Cited

U.S. PATENT DOCUMENTS

2007/0074584 A1* 4/2007 Talarico ................. A61B 17/29
73/856

* cited by examiner

Primary Examiner — Julian W Woo
Assistant Examiner — Bridget E. Rabaglia

(57) ABSTRACT

A method for controlling a laparoscopic instrument. The method includes grasping a target utilizing the laparoscopic instrument by applying an initial trigger force to a trigger of the laparoscopic instrument, obtaining an updated trigger force based on a first pinch force, a second pinch force, and a state of the laparoscopic instrument, and grasping the target utilizing the laparoscopic instrument by applying the updated trigger force to the laparoscopic instrument. The first pinch force is applied to the target by an upper jaw of the laparoscopic instrument and the second pinch force is applied to the target by a lower jaw of the laparoscopic instrument.

9 Claims, 7 Drawing Sheets

100

```
┌─────────────────────────────────────────────────┐
│ Grasping a target by applying an initial trigger force to a │
│       trigger rod of a laparoscopic instrument              │
└─────────────────────────────────────────────────┘ ⎯ 102
                         │
                         ▼
┌─────────────────────────────────────────────────┐
│ Obtaining an updated trigger force based on a first pinch   │
│ force, a second pinch force, and a state of the laparoscopic│
│                       instrument                            │
└─────────────────────────────────────────────────┘ ⎯ 104
                         │
                         ▼
┌─────────────────────────────────────────────────┐
│ Grasping the target by applying the updated trigger force   │
│              to the laparoscopic instrument                 │
└─────────────────────────────────────────────────┘ ⎯ 106
```

FIG. 1A

CONTROLLING A LAPAROSCOPIC INSTRUMENT

CROSS-REFERENCE TO RELATED APPLICATION

This application claims the benefit of priority from U.S. Provisional Patent Application Ser. No. 62/824,327, filed on Mar. 27, 2019, which is incorporated herein by reference in its entirety.

TECHNICAL FIELD

The present disclosure generally relates to minimally invasive medical procedures, and more particularly, to a method and a system for controlling a laparoscopic instrument.

BACKGROUND

Robotic-assisted minimally invasive surgery has numerous advantages such as improved dexterity and ergonomics compared to open and laparoscopic surgeries. For example, surgical robots may filter out a surgeon's hand tremors and scale down his/her hand movements to provide fine movements at a tip of a surgical instrument. However, in comparison with open surgery, robotic and laparoscopic systems may prevent a surgeon from directly touching a tissue and perceiving an interaction force between the tissue and a surgical instrument. Also, there may be no force-sensing unit on patient sides of commercially available surgical robots to capture interaction forces. Thus, lack of haptic feedback may prevent a surgeon from safely grasping and manipulating delicate tissues and organs which may also increase danger of tissue damage or slippage during surgery.

There are two approaches to improve grasping capability of a surgical robot. The first one is a non-auto grasping method and the second one is an auto grasping method. In surgical robots with non-auto grasping method, a position of an instrument jaw may be directly controlled by a surgeon and an interaction force between a tissue and the instrument may be captured by a proximal or distal force/torque sensor. However, forces at instrument jaws may not be accurately transmitted to a surgeon's hands. Thus, it may lead to a tissue damage or slippage during surgery.

In an auto grasping method, an auxiliary control system may prevent a tissue damage and slippage through automatic adjustment of pinch force based on a pull force extended on a tissue. In both methods, it may be needed to measure pinch and pull forces applied to a tissue or organ which, typically, is implemented through a distal force sensing technique or a proximal force sensing technique. In distal force sensing technique, a miniaturized six-degree of freedom force/torque sensor may be installed at a distal end of an instrument to capture pull forces. In addition, one or two miniaturized force sensors located on jaws may measure pinch forces. This technique may lead to some negative issues. For example, its implementation may be challenging since force/torque sensors need to meet limited space, durability, and biocompatibility requirements. In proximal force sensing technique, a six-degree of freedom force/torque sensor may be installed at an end of an instrument, next to a trigger rod, to measure pull forces and a one-degree of freedom force sensor may be installed on the trigger rod to measure pinch forces. This technique does not have the limitations of a distal force sensing technique(e.g., challenging implementation) and also may make it possible to keep the cost low.

The auto grasping methods are based on an assumption that the pinch force magnitudes at each side of jaws are equal during a tissue grasping. With this assumption, a pull force direction is in the same direction as an instrument's rod. However, this condition is very rare, and usually, the pinch force magnitudes of jaws are unequal during general three-dimensional maneuvers.

There is, therefore, a need for auto grasping methods and systems, in which pinch force magnitudes at each of jaws during changing pull force direction are taken into account. There is further a need for auto grasping methods and systems in which damage and slippage of tissue and sensitive organs during surgery are reduced.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure describes an exemplary method for controlling a laparoscopic instrument. An exemplary method may include grasping a target utilizing the laparoscopic instrument by applying an initial trigger force to a trigger of the laparoscopic instrument, obtaining an updated trigger force based on a first pinch force, a second pinch force, and a state of the laparoscopic instrument, and grasping the target utilizing the laparoscopic instrument by applying the updated trigger force to the laparoscopic instrument.

In an exemplary embodiment, the first pinch force may be applied to the target by an upper jaw of the laparoscopic instrument and the second pinch force may be applied to the target by a lower jaw of the laparoscopic instrument. In an exemplary embodiment, the first pinch force may be equal to or larger than the second pinch force.

In an exemplary embodiment, obtaining the updated trigger force based on the first pinch force, the second pinch force, and the state of the laparoscopic instrument may include measuring, utilizing a force sensor, a pull force applied to the target responsive to applying the initial trigger force, the pull force associated with objects connected to the target, extracting, utilizing one or more processors, a lower limit for the second pinch force and an upper limit for the first pinch force utilizing a three-zone grasp model associated with the pull force, setting, utilizing the one or more processors, a magnitude of the second pinch force equal to the lower limit, calculating, utilizing the one or more processors, a magnitude of the first pinch force based on the second pinch force and the pull force, generating, utilizing the one or more processors, a warning alarm responsive to the magnitude of the first pinch force equal to or larger than the upper limit, calculating, utilizing the one or more processors, an average pinch force based on the first pinch force and the second pinch force responsive to the magnitude of the first pinch force smaller than the upper limit, and calculating, utilizing the one or more processors, the updated trigger force based on an inverse force model associated with the average pinch force and the state of the laparoscopic instrument.

In an exemplary embodiment, measuring the pull force may include measuring a magnitude of the pull force and measuring a pull force angle comprising an angle between a direction of the pull force and a bisector of a jaw angle. In an exemplary embodiment, the jaw angle may include an angle between a direction of the upper jaw and a direction of the lower jaw.

In an exemplary embodiment, extracting the lower limit and the upper limit may include generating the three-zone grasp model, for a specific pull force direction, by generating a pinch-pull plane and dividing the pinch-pull plane into three separate zones.

In an exemplary embodiment, the pinch-pull plane, at the specific pull force direction, may include a horizontal axis associated with a magnitude of the pull force and a vertical axis associated with a magnitude of the first pinch force and a magnitude of the second pinch force. In an exemplary embodiment, the vertical axis may be perpendicular to the horizontal axis.

In an exemplary embodiment, the pinch-pull plane into three separate zones may include a slip zone limited to a slip curve, a damage zone limited to a damage curve, and a safe zone limited to the slip curve and the damage curve. In an exemplary embodiment, the safe zone may be associated with the lower limit and the upper limit.

In an exemplary embodiment, dividing the pinch-pull plane into the three separate zones may include deriving the slip curve at the specific pull force direction through replacing the target with a test object, sequentially setting a magnitude of the second pinch force to a plurality of pinch force levels in an ascending order, obtaining a respective slip threshold of a plurality of slip thresholds for each of the plurality of pinch force levels, and obtaining the slip curve by fitting a curve to variations of the plurality of slip thresholds with respect to variations of the plurality of pinch force levels.

In an exemplary embodiment, dividing the pinch-pull plane into the three separate zones may further include deriving the damage curve at the specific pull force direction through sequentially setting the magnitude of the pull force to a plurality of pull force levels in an ascending order, obtaining a respective damage threshold of a plurality of damage thresholds for each of the plurality of pull force levels, and obtaining the damage curve by fitting a curve to variations of the plurality of damage thresholds with respect to variations of the plurality of pull force levels.

In an exemplary embodiment, obtaining a respective damage threshold of a plurality of damage thresholds for each of the plurality of pull force levels may include setting the magnitude of the first pinch force to zero, increasing the magnitude of the first pinch force until a damaged area is generated on the test object, and obtaining the respective damage threshold by measuring the magnitude of the first pinch force responsive to the damaged area being generated. The respective damage threshold may be associated with a given pull force direction and magnitude.

In an exemplary embodiment, calculating the magnitude of the first pinch force based on the second pinch force and the pull force may include solving a static rotational equilibrium equation defined by the following:

$$F_{g1} - F_{g2} = F'_{pull}$$

where:
$F_{g1}$ is a magnitude of the first pinch force,
$F_{g2}$ is a magnitude of the second pinch force, and
$F'_{pull}$ is the magnitude of the pull force along an axis perpendicular to the bisector of the jaw angle.

In an exemplary embodiment, calculating the average pinch force based on the first pinch force and the second pinch force may include averaging the magnitude of the first pinch force and the magnitude of the second pinch force.

In an exemplary embodiment, calculating the updated trigger force may include obtaining the state of the laparoscopic instrument by measuring a jaw angle including an angle between a direction of the upper jaw and a direction of the lower jaw and measuring a wrist angle including an angle between a direction of a rod of the laparoscopic instrument and a bisector of the jaw angle. In an exemplary embodiment, the wrist angle may be defined by the following:

$$\varphi = \cos^{-1}(|\cos\psi| \times |\cos\alpha|)$$

where:
$\varphi$ is the wrist angle,
$\psi$ is an amount of rotation of the laparoscopic instrument around a Y axis, and
$\alpha$ is an amount of rotation of the laparoscopic instrument around a Z axis.

In an exemplary embodiment, calculating the updated trigger force may further include calculating the updated trigger force according to an operation defined by the following:

$$F_t = g^*(F_g, \theta, \varphi)$$

where:
$F_g$ is the average pinch force,
$F_t$ is the updated trigger force,
$\theta$ is the jaw angle,
$\varphi$ is the wrist angle, and
$g^*(.;;)$ is the inverse of the instrument force model of the laparoscopic instrument.

In an exemplary embodiment, calculating the updated trigger force may further include pivotally connecting the upper jaw and the lower jaw by a pivot, applying the initial trigger force to the laparoscopic instrument by exerting the initial trigger force to an actuation cable associated with the laparoscopic instrument, grasping the target at a contact point of the target by applying the initial trigger force to the laparoscopic instrument, and obtaining the force model according to a set of equations defined by the following:

$$|\vec{F}_g| = \frac{(|\vec{F}_t| - f_{k0}) \times 0.5}{e^{\varphi(\mu')}} \times \frac{\left[\left(\frac{L}{\sin(0.5\theta + \alpha_0)} \times \cos(0.5\theta + \alpha_0)\right) - \mu(L + r)\right]}{d \times (\sin(0.5\theta + \alpha_0) + \mu\cos(0.5\theta + \alpha_0))}$$

$$\theta = 2 \times \sin^{-1}\left(\frac{L}{D - \left(x_{cable} - \frac{|\vec{F}_t|}{K_{inst}}\right)} - \alpha_0\right)$$

$$\mu' = 0.5\mu_1 + \mu_2$$

where:
$|\vec{F}_g|$ is a magnitude of the average pinch force,
$|\vec{F}_t|$ is a magnitude of the updated trigger force,
$f_{k0}$ is a static friction of the laparoscopic instrument,
$L$, $\alpha_0$, and $D$ are geometrical parameters of the laparoscopic instrument,
$\mu$ is a friction coefficient between a pin of the laparoscopic instrument and a cam slot of the lower jaw and the upper jaw,
$r$ is a radius of the pin,
$d$ is a distance between the pivot and the contact point,
$K_{inst}$ is a stiffness of the laparoscopic instrument,
$\mu_1$ is a friction coefficient between the actuation cable and an inner side of the instrument rod, and $\mu_2$ is a friction coefficient between the actuation cable and an inner side of the instrument wrist.

In another aspect of the present disclosure, a system for controlling a laparoscopic instrument is disclosed. An exemplary system may include an actuator comprising an actuation cable configured to apply a trigger force to a trigger associated with the laparoscopic instrument. In an exemplary embodiment, the laparoscopic instrument may be configured to grasp a target at a contact point of the target responsive to application of the trigger force.

In an exemplary embodiment, the laparoscopic instrument may include a lower jaw, an upper jaw, a jaw angle, and a wrist angle. In an exemplary embodiment, the upper jaw and the lower jaw may be connected pivotally utilizing a pivot. In an exemplary embodiment, the jaw angle may include an angle between a direction of the upper jaw and a direction of the lower jaw. In an exemplary embodiment, the wrist angle may include an angle between a direction of the rod and a bisector of the jaw angle. In an exemplary embodiment, the wrist angle may be defined by the following:

$$\varphi = \cos^{-1}(|\cos \psi| \times |\cos \alpha|)$$

where:
$\varphi$ is the wrist angle,
$\psi$ is an amount of rotation of the laparoscopic instrument around a Y axis, and
$\alpha$ is an amount of rotation of the laparoscopic instrument around a Z axis.

In an exemplary embodiment, the system may further include a memory having processor-readable instructions stored therein and one or more processors configured to access the memory and execute the processor-readable instructions, which, when executed by the processor may configure the processor to perform a method. In an exemplary embodiment, the method may include updating a magnitude of the trigger force based on a first pinch force, a second pinch force, and a state of the laparoscopic instrument.

In an exemplary embodiment, the system may further include a six degree of freedom force/torque sensor installed at an end of the laparoscopic instrument next to a trigger of the system. The six degree of freedom force/torque sensor may be configured to measure a magnitude of a pull force and a direction of the pull force. In an exemplary embodiment, the pull force may be applied to the target responsive to application of the trigger force. In an exemplary embodiment, the pull force may be associated with objects connected to the target. In an exemplary embodiment, system may further include a one degree of freedom force sensor which may be installed on a trigger rod of laparoscopic instrument. In an exemplary embodiment, the one degree of freedom force sensor may be configured to obtain the pinch force based on the proximal force-sensing technique. In an exemplary embodiment, the system may further include a spherical mechanism configured to measure a wrist angle of the laparoscopic instrument.

In an exemplary embodiment, updating the magnitude of the trigger force based on the first pinch force, a second pinch force, and a state of the laparoscopic instrument may include extracting a lower limit for the second pinch force and an upper limit for second pinch force utilizing a three-zone grasp model associated with the pull force, setting a magnitude of the second pinch force equal to the lower limit, calculating a magnitude of the first pinch force based on the second pinch force, the magnitude of the pull force, and the pull force direction, generating a warning alarm responsive to the magnitude of the first pinch force equal to or larger than the upper limit, calculating an average pinch force based on the first pinch force and the second pinch force, and calculating an updated value for the magnitude of the trigger force based on an inverse force model associated with the average pinch force and the state of the laparoscopic instrument.

In an exemplary embodiment, extracting the lower limit and the upper limit may include generating the three-zone grasp model for a specific pull force direction by generating a pinch-pull plane comprising a plurality of pairs and dividing the pinch-pull plane into three separate zones. In an exemplary embodiment, at a specific pull force direction, each of the plurality of pairs may include a first value associated with the magnitude of the pull force and a second value associated with a magnitude of the first pinch force and the magnitude of the second pinch force.

In an exemplary embodiment, the pinch-pull plane may include a slip zone limited to a slip curve, a damage zone limited to a damage curve, and a safe zone limited to the slip curve and the damage curve. In an exemplary embodiment, the safe zone may be associated with the lower limit and the upper limit.

In an exemplary embodiment, dividing the pinch-pull plane into the three separate zones may include deriving the slip curve at a specific pull force direction by replacing the target with a test object, sequentially setting a magnitude of the second pinch force to a plurality of pinch force levels in an ascending order, obtaining a respective slip threshold of a plurality of slip thresholds for each of the plurality of pinch force levels, and obtaining the slip curve by fitting a curve to variations of the plurality of slip thresholds with respect to variations of the plurality of pinch force levels.

In an exemplary embodiment, obtaining the respective slip threshold of the plurality of slip thresholds for each of the plurality of pinch force levels may include setting the magnitude of the pull force to zero, increasing the magnitude of the pull force until the test object is slipped from the laparoscopic instrument, and obtaining the respective slip threshold by measuring the magnitude of the pull force responsive to the test object being slipped.

In an exemplary embodiment, dividing the pinch-pull plane into the three separate zones may further include deriving the damage curve at the specific pull force direction by sequentially setting the magnitude of the pull force to a plurality of pull force levels in an ascending order, obtaining a respective damage threshold of a plurality of damage thresholds for each of the plurality of pull force levels, and obtaining the damage curve by fitting a curve to variations of the plurality of damage thresholds with respect to variations of the plurality of pull force levels.

In an exemplary embodiment, obtaining a respective damage threshold of a plurality of damage thresholds for each of the plurality of pull force levels may include setting the magnitude of the first pinch force to zero, increasing the magnitude of the first pinch force until a damaged area is generated on the test object, and obtaining the respective damage threshold by measuring the magnitude of the first pinch force responsive to the damaged area being generated. The respective damage threshold may be associated with a given pull force magnitude and direction.

In an exemplary embodiment, calculating the magnitude of the first pinch force may include solving a static rotational equilibrium equation defined by the following:

$$F_{g1} - F_{g2} = F'_{pull}$$

where:
$F_{g1}$ is a magnitude of the first pinch force, $F_{g2}$ is a magnitude of the second pinch force, and
$F'_{pull}$ is the magnitude of the pull force along an axis perpendicular to the bisector of the jaw angle.

In an exemplary embodiment, calculating the average pinch force may include averaging the magnitude of the first pinch force and the magnitude of the second pinch force. In an exemplary embodiment, calculating the updated value for the magnitude of the trigger force based on the inverse force model may include obtaining the inverse force model according to a set of equations of the instrument force model defined by the following:

$$|\vec{F}_g| = \frac{(|\vec{F}_t| - f_{k0}) \times 0.5}{e^{\varphi(\mu')}} \times \frac{\left[\left(\frac{L}{\sin(0.5\theta + \alpha_0)} \times \cos(0.5\theta + \alpha_0)\right) - \mu(L+r)\right]}{d \times (\sin(0.5\theta + \alpha_0) + \mu\cos(0.5\theta + \alpha_0))}$$

$$\theta = 2 \times \sin^{-1}\left(\frac{L}{D - \left(x_{cable} - \frac{|\vec{F}_t|}{K_{inst}}\right)} - \alpha_0\right)$$

$$\mu' = 0.5\mu_1 + \mu_2$$

where:
$|\vec{F}_g|$ is a magnitude of the average pinch force,
$|\vec{F}_t|$ is the updated value for the magnitude of the trigger force,
$f_{k0}$ is a static friction of the laparoscopic instrument,
$\theta$ is the jaw angle,
$\varphi$ is the wrist angle,
L, $\alpha_0$, and D are geometrical parameters of the laparoscopic instrument,
$\mu$ is a friction coefficient between a pin of the laparoscopic instrument and a cam slot of the lower jaw and the upper jaw,
r is a radius of the pin,
d is a distance between the pivot and the contact point,
$K_{inst}$ is a stiffness of the laparoscopic instrument,
$\mu_1$ is a friction coefficient between the actuation cable and an inner side of the instrument rod, and
$\mu_2$ is a friction coefficient between the actuation cable and an inner side of the instrument wrist.

BRIEF DESCRIPTION OF THE DRAWINGS

The drawing figures depict one or more implementations in accord with the present teachings, by way of example only, not by way of limitation. In the figures, like reference numerals refer to the same or similar elements.

FIG. 1A illustrates a flowchart of a method for controlling a laparoscopic instrument, consistent with one or more exemplary embodiments of the present disclosure.

DETAILED DESCRIPTION

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings.

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

Herein is disclosed an exemplary method and system for controlling a laparoscopic instrument. According to an exemplary method, a tissue of a human body may be grasped by applying an initial trigger force to a trigger of a laparoscopic instrument. When the tissue is grasped by jaws of the laparoscopic instrument, a force applied to an upper jaw of the laparoscopic instrument from the tissue and a force applied to a lower jaw of the laparoscopic instrument from the tissue may be different. Then, an updated trigger force of a laparoscopic instrument may be obtained based on different forces applied to jaws of the laparoscopic instrument from the tissue. Then, the tissue may be grasped by applying the obtained updated trigger force to the trigger of the laparoscopic instrument.

FIG. 1A shows a flowchart of a method for controlling a laparoscopic instrument, consistent with one or more exemplary embodiments of the present disclosure. An exemplary method 100 may include grasping a target utilizing a laparoscopic instrument by applying an initial trigger force to a trigger of the laparoscopic instrument (step 102), obtaining an updated trigger force based on a first pinch force, a second pinch force, and a state of the laparoscopic instrument (step 104), and grasping the target utilizing the laparoscopic instrument by applying the updated trigger force to the laparoscopic instrument (step 106).

Figure 2A:
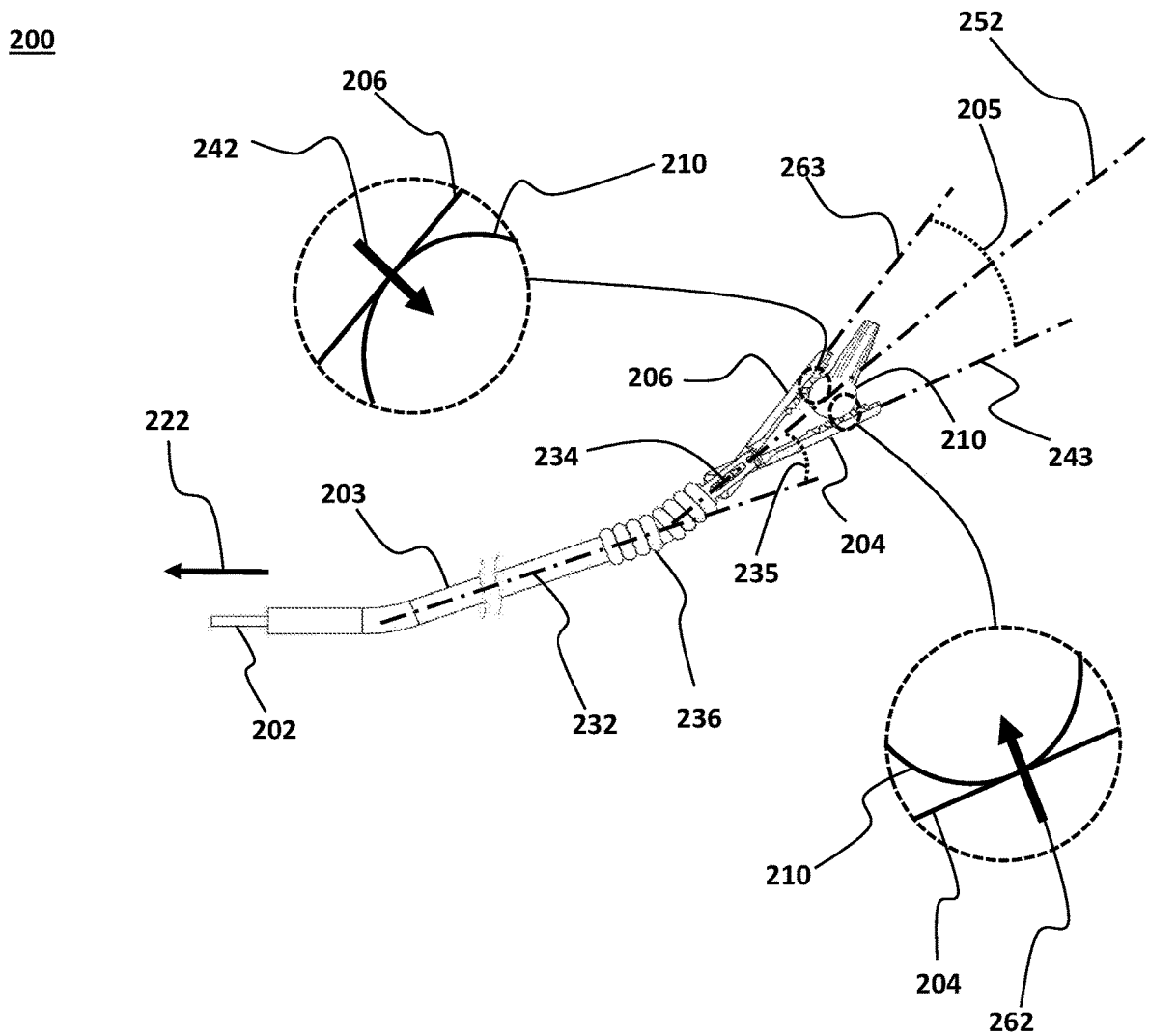
FIG. 2A illustrates a schematic of a laparoscopic instrument, consistent with one or more exemplary embodiments of the present disclosure.
Figure 2B:
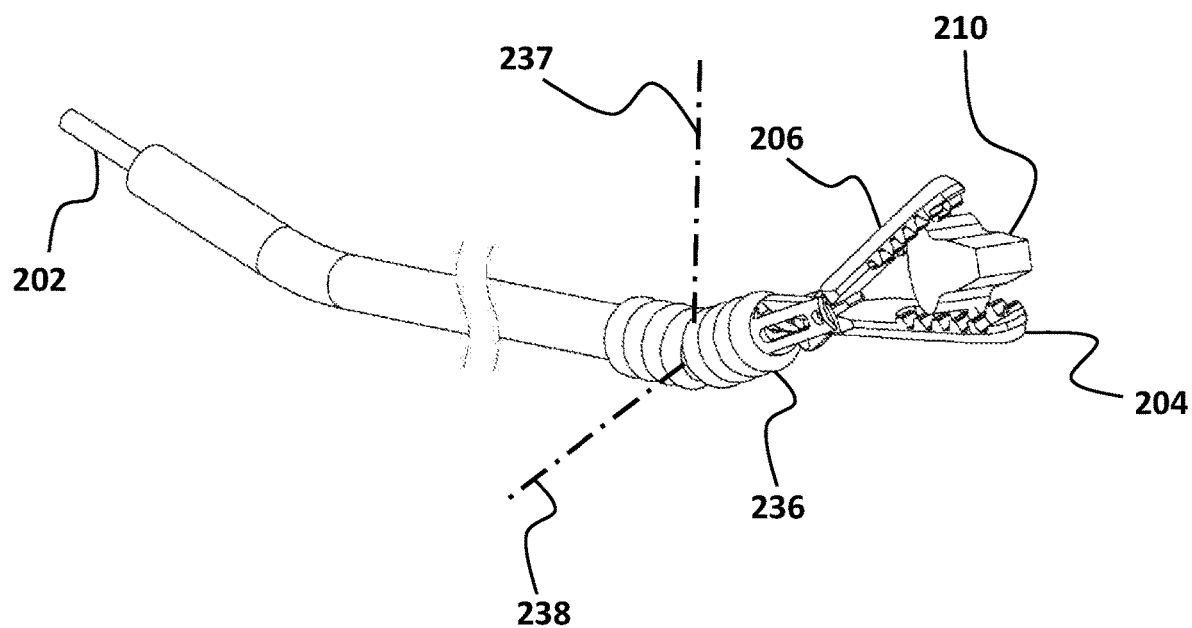
FIG. 2B illustrates another schematic of a laparoscopic instrument, consistent with one or more exemplary embodiments of the present disclosure.

FIG. 2A shows a schematic of a laparoscopic instrument, consistent with one or more exemplary embodiments of the present disclosure. FIG. 2B shows another schematic of a laparoscopic instrument, consistent with one or more exemplary embodiments of the present disclosure. In an exemplary embodiment, different steps of method 100 may be implemented by utilizing an exemplary laparoscopic instrument 200. In an exemplary embodiment, laparoscopic instrument 200 may include a actuation cable 202 and a rod 203. In an exemplary embodiment, a target 210 may be grasped by applying a force to actuation cable 202. In an exemplary embodiment, a force may be applied to actuation cable 202. In an exemplary embodiment, a surgeon may apply force to a trigger of a laparoscopic instrument manually. However, in an exemplary embodiment, a force may be applied to a trigger of a laparoscopic instrument by utilizing an actuator. In an exemplary embodiment, target 210 may include a tissue or an organ in a human body. In an exemplary embodiment, a user, by utilizing laparoscopic instrument 200, may grasp target 210 by pulling actuation cable 202 in a direction 222.

In an exemplary embodiment, it may be understood that by applying the initial trigger force to actuation cable 202, a pull force may be applied to target 210 due to the fact that target 210 may be connected to some objects near target 210. In an exemplary embodiment, it may be understood that the pull force may be along any direction in the space. In an exemplary embodiment, it may be understood that target 210 may be connected to some tissues and/or organs in a human body. For example, target 210 may be connected to a bone and/or a muscle of the human body. when the initial trigger force is applied to actuation cable 202, objects connected to target 210 may resist against this force, and consequently, a pull force may be applied to target 210. In an exemplary embodiment, the applied pull force may be along any direction in the space. In an exemplary embodiment, laparoscopic instrument 200 may further include a lower jaw 204 and an upper jaw 206. In an exemplary embodiment, lower jaw 204 and upper jaw 206 may be connected pivotally by utilizing a pin 234. In an exemplary embodiment, when target 210 is grasped by laparoscopic instrument 200, a first pinch force 242 may be applied to target 210 from upper jaw 206 and a second pinch force 262 may be applied to target 210 from lower jaw 204. In an exemplary embodiment, it may be understood that when target 210 is grasped by laparoscopic instrument 200, lower jaw 204 and upper jaw 206 may hold target 210 between lower jaw 204 and upper jaw 206 in such a way that target 210 is prevented from slipping. In an exemplary embodiment, first pinch force 242 may refer to a force upper jaw 206 applies to target 210 when target 210 is grasped by laparoscopic instrument 200. In an exemplary embodiment, second pinch force 262 may refer to a force lower jaw 204 applies to target 210 when target 210 is grasped by laparoscopic instrument 200. As second pinch force 262 may be different from first pinch force 242, in an exemplary embodiment, it may be assumed that first pinch force 242 may be equal to or larger than second pinch force 262. In an exemplary embodiment, a jaw angle 205 may be defined as an angle between a main axis 243 of lower jaw 204 and a main axis 263 of upper jaw 206. Also, a wrist angle 235 may be defined as an angle between a main axis 232 of rod 203 and a bisector 252 of jaw angle 205. In an exemplary embodiment, wrist angle 235 may be defined by the following:

$$\varphi = \cos^{-1}(|\cos \psi| \times |\cos \alpha|)$$

where:
$\varphi$ is the wrist angle,
$\psi$ is an amount of rotation of laparoscopic instrument 200 around a Y axis 237, and
$\alpha$ is an amount of rotation of the laparoscopic instrument around a Z axis 238.

In an exemplary embodiment, the state of laparoscopic instrument 200 may refer to a status of jaw angle 205 and wrist angle 235. In an exemplary embodiment, different measures of jaw angle 205 and wrist angle 235 may lead to different states of laparoscopic instrument 200. For example, by increasing and/or decreasing of jaw angle 205 and/or wrist angle 235, state of laparoscopic instrument 200 may change. In other words, each specific state of laparoscopic instrument 200 may refer to a specific measure of jaw angle 205 and wrist angle 235.

Figure 1B:
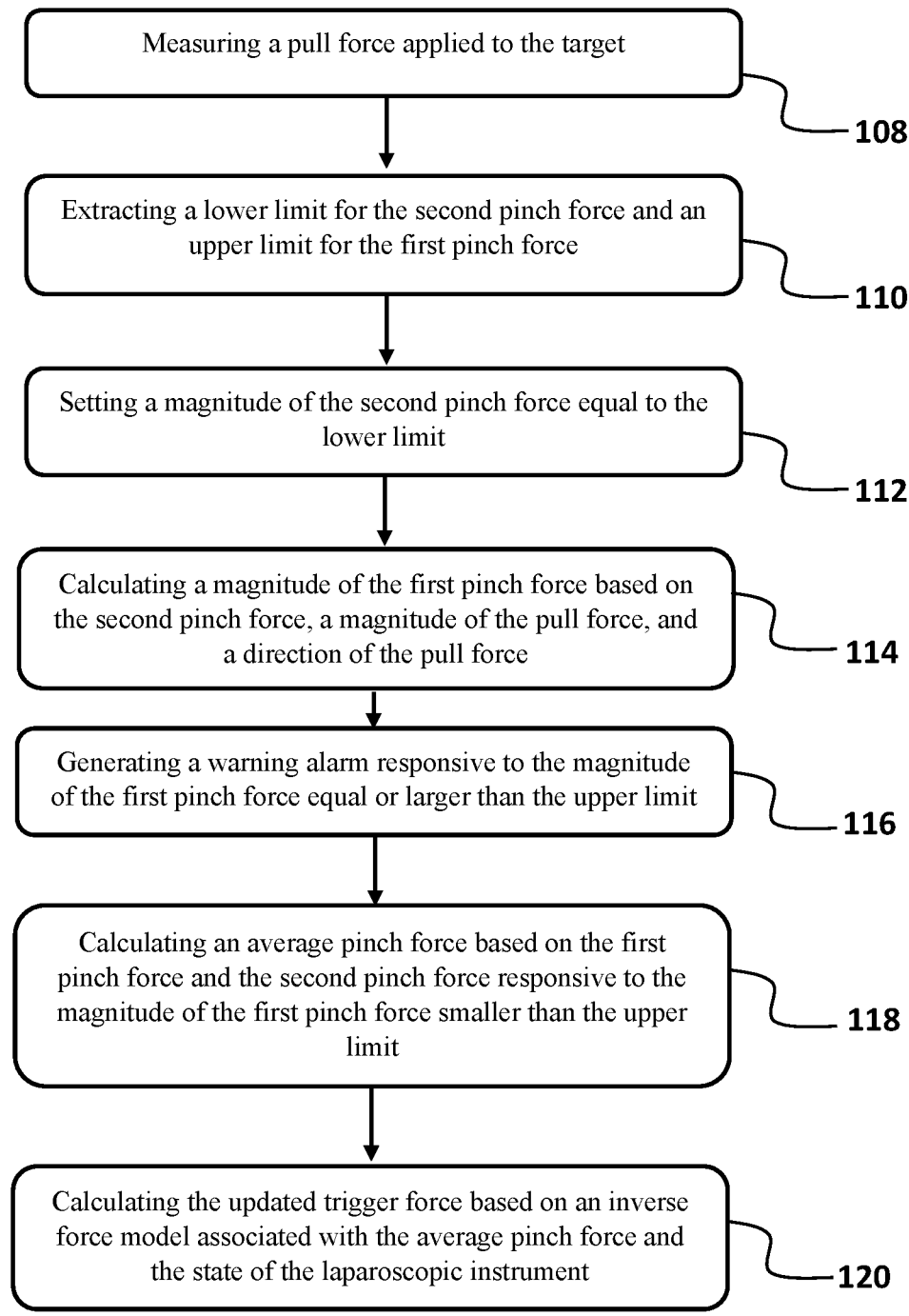
FIG. 1B illustrates a flowchart for obtaining an updated trigger force, consistent with one or more exemplary embodiments of the present disclosure.

In further detail with respect to step 104, FIG. 1B shows a flowchart for obtaining the updated trigger force, consistent with one or more exemplary embodiments of the present disclosure. In an exemplary embodiment, obtaining the updated trigger force may include measuring a pull force magnitude and direction applied to target 210 (step 108), extracting a lower limit for second pinch force 262 and an upper limit for first pinch force 242 (step 110), setting a magnitude of second pinch force 262 equal to the lower limit (step 112), calculating a magnitude of first pinch force 242 based on second pinch force 262 and the pull force magnitude and direction (step 114), generating a warning alarm responsive to the magnitude of first pinch force 262 equal to or larger than the upper limit (step 116), calculating an average pinch force based on first pinch force 242 and second pinch force 262 responsive to the magnitude of first pinch force 262 smaller than the upper limit (step 118), and calculating the updated trigger force based on an inverse force model associated with the first pinch force, the second pinch force, and the state of the laparoscopic instrument (step 120).

In an exemplary embodiment, the pull force applied to target 210 may include a pull force magnitude and a pull force angle. In an exemplary embodiment, the pull force angle may change by changing a direction of the pull force in space. In an exemplary embodiment, the pull force magnitude and the pull force angle may be measured by utilizing a six degree of freedom force/torque sensor which is installed at an end of laparoscopic instrument 200 and next to the trigger. In an exemplary embodiment, the pull force angle may be defined by an angle between a direction of the pull force and bisector 252 of jaw angle 205.

Figure 3:
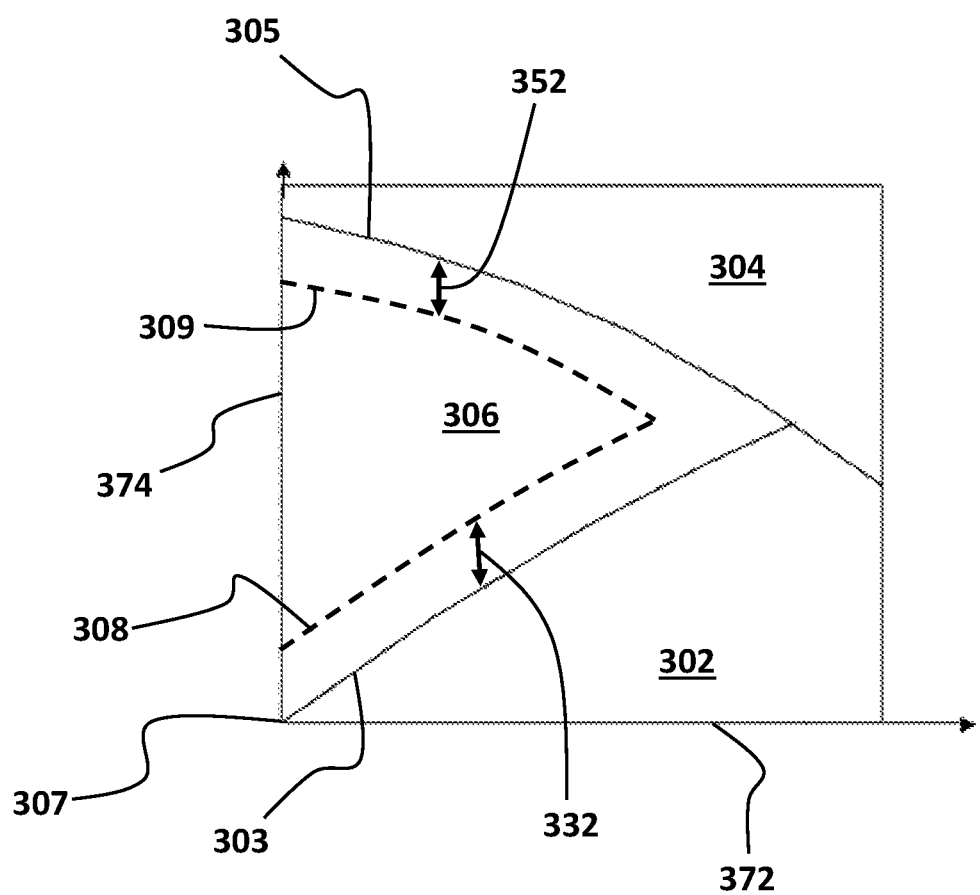
FIG. 3 illustrates a three-zone grasp model, consistent with one or more exemplary embodiments of the present disclosure.

In an exemplary embodiment, extracting a lower limit for second pinch force 262 and an upper limit for first pinch force 242 (step 110) may be implemented by utilizing a three-zone grasp model associated with the pull force. FIG. 3 shows a three-zone grasp model 300, consistent with one or more exemplary embodiments of the present disclosure. in an exemplary embodiment, it may be understood that three-zone grasp model 300 may be associated with a specific direction of the pull force. In fact, for each respective direction of the pull force, a respective three-zone grasp model may be extracted.

As shown in FIG. 3, in an exemplary embodiment, three-zone grasp model 300 for a specific pull force direction may be defined in a pinch-pull plane 307 having a horizontal axis 372 associated with the pull force magnitude. In an exemplary embodiment, pinch-pull plane 307 may also have a vertical axis 374 associated with first pinch force 242 and second pinch force 262. In an exemplary embodiment, pinch-pull plane 307 may be divided into three separate zones including a slip zone 302, a damage zone 304, and a safe zone 306. In an exemplary embodiment, slip zone 302 may be limited to a slip curve 303, damage zone 304 may be limited to a damage curve 305, and safe zone 306 may be limited to slip curve 303 and damage curve 305. In an exemplary embodiment, the lower limit may be associated with slip curve 303 and the upper limit may be associated with damage curve 305.

As further shown in FIG. 3, in an exemplary embodiment, a practical slip curve 308 may be defined by shifting up slip curve 303 by a first amount 332. Furthermore, in an exemplary embodiment, a practical damage curve 309 may be defined by shifting down damage curve 305 by a second amount 352. In an exemplary embodiment, a practical safe zone bounded between practical slip curve 308 and practical damage curve 309 may be defined. In an exemplary embodiment, practical safe zone may help to ensure a safe grasping during an implementation of the auto-grasping algorithm. In an exemplary embodiment, the lower limit may be extracted by utilizing practical slip curve 308. In an exemplary embodiment, the upper limit may be extracted by utilizing practical damage curve 309. In an exemplary embodiment, first amount 332 and second amount 352 may be calculated based on a laparoscopic surgery conditions. In an exemplary embodiment, first amount 332 and second amount 352 may be the same.

In an exemplary embodiment, in order to derive slip curve 303, target 210 may be replaced with a test object. In an exemplary embodiment, the test object may be similar in shape, size, and mechanical properties with target 210. Then, a magnitude of second pinch force 262 may be sequentially set to a plurality of pinch force levels in an ascending order which may start from zero. Then, for each pinch force level of plurality of pinch force levels, the magnitude of the pull force at a specific pull force direction may be increased until the test object is slipped from laparoscopic instrument 200. In an exemplary embodiment, slipping the test object from laparoscopic instrument 200 may refer to exiting the test object from laparoscopic instrument 200 when the test target is grasped by laparoscopic instrument 200 due to insufficient grasp force. In an exemplary embodiment, the pull force at which the test object started slipping out from lower jaw 204 and upper jaw 206 may be recorded as a slip data point associated with a given pinch force magnitude and the pull force direction. Then, a respective slip threshold of a plurality of slip thresholds may be measured responsive to the test object slipping. And finally, slip curve 303 for a specific pull force direction may be obtained by fitting a curve to variations of the plurality of slip thresholds with respect to variations of the plurality of pinch force levels.

In an exemplary embodiment, in order to derive damage curve 305, the magnitude of the pull force at the specific pull force direction may be sequentially set to a plurality of pull force levels in an ascending order which may start from zero. Then, for each of the plurality of pull force levels, the magnitude of first pinch force 242 may be increased until a damage area is generated on the test object. In an exemplary embodiment, the pinch force may be recorded as a damage data point associated with a given magnitude of the pull force and the respective pull force direction. Then, a respective damage threshold from a plurality of damage thresholds may be obtained by measuring the magnitude of first pinch force 242 responsive to the damaged area being generated. And finally, damage curve 305 may be obtained by fitting a curve to variations of the plurality of damage thresholds with respect to variations of the plurality of pull force levels at the specific pull force direction. In an exemplary embodiment, it may be understood that damage curve 305 and slip curve 303 may be associated with the specific pull force direction. In an exemplary embodiment, a respective damage curve 305 and a respective slip curve 303 may be extracted for each respective pull force direction.

In an exemplary embodiment, the pull force applied to target 210 responsive to applying the initial trigger force, may be measured utilizing a force sensor. In an exemplary embodiment, the force sensor may refer to a device that may be able to measure a force applied to a thing. In an exemplary embodiment, the force sensor may include a dynamometer. In an exemplary embodiment, the force sensor may include a six degree of freedom force/torque sensor which is installed at an end of laparoscopic instrument 200 and configured to measure the pull force magnitude and direction. Then, utilizing three-zone grasp model 300, for a given magnitude and a given direction of the pull force, lower limit and upper limit of practically safe pinch forces may be extracted. In an exemplary embodiment, in order to extract the lower limit and the upper limit of practically safe pinch forces, a hypothetical line (not illustrated) parallel to second axis 374 and passing through a point at first axis 372 associated with the measured pull force at a specific pull force direction may be utilized. In an exemplary embodiment, for a specific pull force magnitude and direction, a value of an intersection point of the hypothetical line and practical damage curve 309 may indicate the upper limit and a value of an intersection point of the hypothetical line and practical slip curve 308 may indicate the lower limit. Then, a magnitude of second pinch force 262 may be set to the extracted lower limit and then a magnitude of first pinch force 242 may be calculated based on second pinch force 262, the magnitude of the pull force, and the direction of the pull force.

In an exemplary embodiment, calculating the magnitude of the first pinch force based on the second pinch force and the pull force (step 114) may be implemented by solving a static rotational equilibrium equation defined by the following:

$$F_{g1}F_{g2}=F'_{pull}$$

Where $F_{g1}$ is a magnitude of first pinch force 242, $F_{g2}$ is a magnitude of second pinch force 262, and $F'_{pull}$ is the magnitude of the pull force along an axis perpendicular to bisector 252 of jaw angle 205 which may be measured utilizing a force sensor/dynamometer. In an exemplary embodiment, if the calculated magnitude of first pinch force 242 is equal to or larger than the upper limit, a warning alarm may be generated to show that the total applied force to target 210 may not be allowed. If the magnitude of first pinch force 242 is smaller than the upper limit, an average pinch force may be calculated based on first pinch force 242 and second pinch force 262. In an exemplary embodiment, the average pinch force may be calculated by averaging first pinch force 242 and second pinch force 262. In an exemplary embodiment, the average pinch force may be calculated by averaging the magnitude of first pinch force 242 and the magnitude of second pinch force 262. In an exemplary embodiment, the updated trigger force may be calculated by using an inverse force model of the instrument force model. In an exemplary embodiment, the instrument force model may be defined by the following:

$$|\vec{F}_g| = \frac{(|\vec{F}_t| - f_{k0}) \times 0.5}{e^{\varphi(\mu')}} \times \frac{\left[\left(\frac{L}{\sin(0.5\theta + \alpha_0)} \times \cos(0.5\theta + \alpha_0)\right) - \mu(L+r)\right]}{d \times (\sin(0.5\theta + \alpha_0) + \mu\cos(0.5\theta + \alpha_0))}$$

$$\theta = 2 \times \sin^{-1}\left(\frac{L}{D - \left(x_{cable} - \frac{|\vec{F}_t|}{K_{inst}}\right)} - \alpha_0\right)$$

-continued $$\mu' = 0.5\mu_1 + \mu_2$$

$|\vec{F}_g|$ is a magnitude of the average pinch force. $|\vec{F}_t|$ is a magnitude of the updated trigger force. $f_{k0}$ is a static friction of the laparoscopic instrument. L, $\alpha_0$, and D are geometrical parameters of the laparoscopic instrument, $\mu$ is a friction coefficient between pin 234 of laparoscopic instrument 200 and a cam slot of lower jaw 204 and upper jaw 206, r is a radius of pin 234, d is a distance between the pivot and a contact point. In an exemplary embodiment, contact point may refer to a point at which target 210 is in contact with lower jaw 204 and upper jaw 206. $K_{inst}$ is a stiffness of laparoscopic instrument 200, $\mu_1$ is a friction coefficient between the actuation cable and an inner side of the instrument rod, and $\mu_2$ is a friction coefficient between the actuation cable and an inner side of an instrument wrist.

Figure 4:
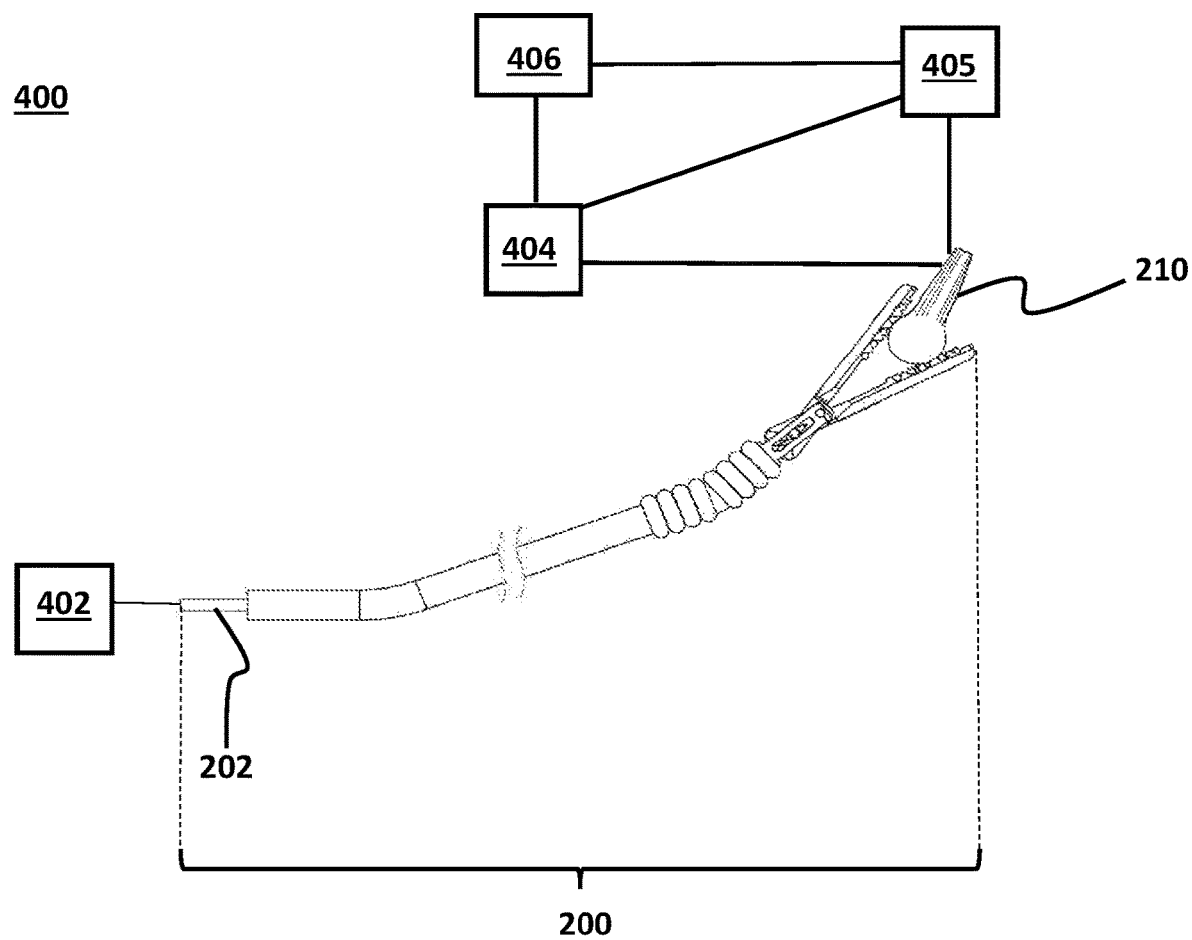
FIG. 4 illustrates a system for controlling a laparoscopic instrument, consistent with one or more exemplary embodiments of the present disclosure.

Herein is also disclosed an exemplary system for controlling a laparoscopic instrument for example laparoscopic instrument 200. FIG. 4 shows a system 400 for controlling laparoscopic instrument 200, consistent with one or more exemplary embodiments of the present disclosure. In an exemplary embodiment, system 400 may include an actuator 402 including an actuation cable 202. In an exemplary embodiment, actuation cable 202 may be configured to apply a trigger force to laparoscopic instrument 200. In an exemplary embodiment, system 400 may further include a memory 404 having processor-readable instructions stored therein. In an exemplary embodiment, system 400 may further include one or more processors 406 configured to access memory 404 and execute the processor-readable instructions, which, when executed by the processor configures the processor to perform a method with similar steps and details as method 100. In an exemplary embodiment, system 400 may further include a force sensor 405 configured to measure a magnitude of the pull force and a direction of the pull force. In an exemplary embodiment, system 400 may further include a 6-degree of freedom force/torque sensor which may be installed next to the trigger of laparoscopic instrument 200. In an exemplary embodiment, six degree of freedom force/torque sensor may be configured to measure the pull force magnitude and direction. In an exemplary embodiment, system 400 may further include a one degree of freedom force sensor which may be installed on a trigger rod of laparoscopic instrument 200. In an exemplary embodiment, the one degree of freedom force sensor may be configured to measure the pinch force based on a proximal force-sensing technique. In an exemplary embodiment, the proximal force-sensing technique may refer to a technique that calculate the pinch force based on an instrument force model and a force applied to the trigger rod. In an exemplary embodiment, system 400 may further include a spherical mechanism including a plurality of actuations' encoders. In an exemplary embodiment, actuation's encoders of the spherical mechanism may be configured to measure the wrist angle.

Figure 5:
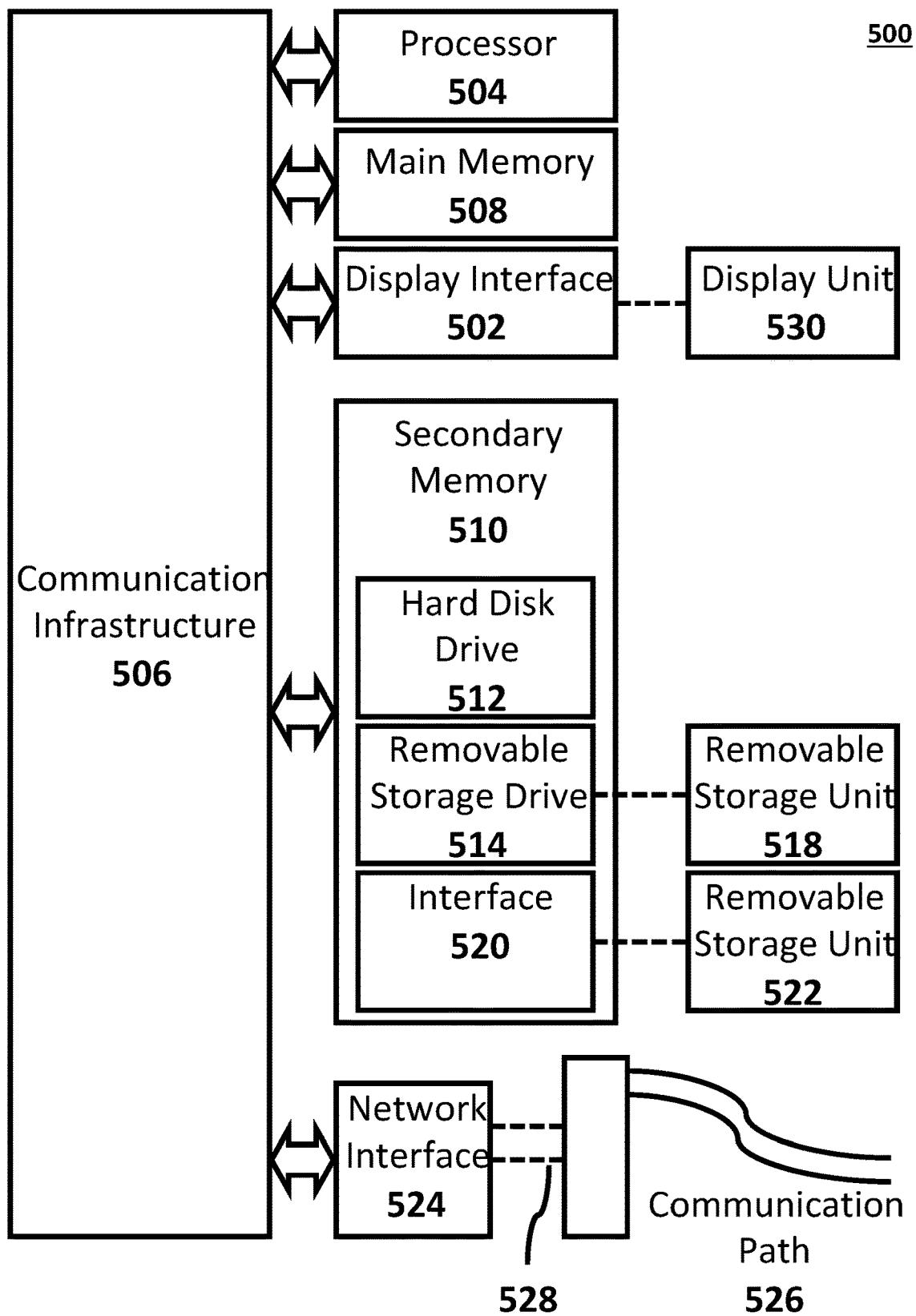
FIG. 5 illustrates an example computer system in which an embodiment of the present invention, or portions thereof, may be implemented as computer-readable code, consistent with exemplary embodiments of the present disclosure.

FIG. 5 shows an example computer system 500 in which an embodiment of the present invention, or portions thereof, may be implemented as computer-readable code, consistent with exemplary embodiments of the present disclosure. For example, method 100 may be implemented in computer system 500 using hardware, software, firmware, tangible computer readable media having instructions stored thereon, or a combination thereof and may be implemented in one or more computer systems or other processing systems. In an exemplary embodiment, system 500 may be analogous to processor 406. Hardware, software, or any combination of such may embody any of the modules and components in FIG. 4.

If programmable logic is used, such logic may execute on a commercially available processing platform or a special purpose device. One ordinary skill in the art may appreciate that an embodiment of the disclosed subject matter can be practiced with various computer system configurations, including multi-core multiprocessor systems, minicomputers, mainframe computers, computers linked or clustered with distributed functions, as well as pervasive or miniature computers that may be embedded into virtually any device.

For instance, a computing device having at least one processor device and a memory may be used to implement the above-described embodiments. A processor device may be a single processor, a plurality of processors, or combinations thereof. Processor devices may have one or more processor "cores."

An embodiment of the invention is described in terms of this example computer system 500. After reading this description, it will become apparent to a person skilled in the relevant art how to implement the invention using other computer systems and/or computer architectures. Although operations may be described as a sequential process, some of the operations may in fact be performed in parallel, concurrently, and/or in a distributed environment, and with program code stored locally or remotely for access by single or multi-processor machines. In addition, in some embodiments the order of operations may be rearranged without departing from the spirit of the disclosed subject matter.

Processor device 504 may be a special purpose or a general-purpose processor device. As will be appreciated by persons skilled in the relevant art, processor device 504 may also be a single processor in a multi-core/multiprocessor system, such system operating alone, or in a cluster of computing devices operating in a cluster or server farm. Processor device 504 may be connected to a communication infrastructure 506, for example, a bus, message queue, network, or multi-core message-passing scheme.

In an exemplary embodiment, computer system 500 may include a display interface 502, for example a video connector, to transfer data to a display unit 530, for example, a monitor. Computer system 500 may also include a main memory 508, for example, random access memory (RAM), and may also include a secondary memory 510. Secondary memory 510 may include, for example, a hard disk drive 512, and a removable storage drive 514. Removable storage drive 514 may include a floppy disk drive, a magnetic tape drive, an optical disk drive, a flash memory, or the like. Removable storage drive 514 may read from and/or write to a removable storage unit 518 in a well-known manner. Removable storage unit 518 may include a floppy disk, a magnetic tape, an optical disk, etc., which may be read by and written to by removable storage drive 514. As will be appreciated by persons skilled in the relevant art, removable storage unit 518 may include a computer usable storage medium having stored therein computer software and/or data.

In alternative implementations, secondary memory 510 may include other similar means for allowing computer programs or other instructions to be loaded into computer system 500. Such means may include, for example, a removable storage unit 522 and an interface 520. Examples of such means may include a program cartridge and cartridge interface (such as that found in video game devices), a removable memory chip (such as an EPROM, or PROM)

and associated socket, and other removable storage units 522 and interfaces 520 which allow software and data to be transferred from removable storage unit 522 to computer system 500.

Computer system 500 may also include a communications interface 524. Communications interface 524 allows software and data to be transferred between computer system 500 and external devices. Communications interface 524 may include a modem, a network interface (such as an Ethernet card), a communications port, a PCMCIA slot and card, or the like. Software and data transferred via communications interface 524 may be in the form of signals, which may be electronic, electromagnetic, optical, or other signals capable of being received by communications interface 524. These signals may be provided to communications interface 524 via a communications path 526. Communications path 526 carries signals and may be implemented using wire or cable, fiber optics, a phone line, a cellular phone link, an RF link or other communications channels.

In this document, the terms "computer program medium" and "computer usable medium" are used to generally refer to media such as removable storage unit 518, removable storage unit 522, and a hard disk installed in hard disk drive 512. Computer program medium and computer usable medium may also refer to memories, such as main memory 508 and secondary memory 510, which may be memory semiconductors (e.g. DRAMs, etc.).

Computer programs (also called computer control logic) are stored in main memory 508 and/or secondary memory 510. Computer programs may also be received via communications interface 524. Such computer programs, when executed, enable computer system 500 to implement different embodiments of the present disclosure as discussed herein. In particular, the computer programs, when executed, enable processor device 504 to implement the processes of the present disclosure, such as the operations in method 100 illustrated by flowchart 100 of FIG. 1A and flowchart 104 of FIG. 1B discussed above. Accordingly, such computer programs represent controllers of computer system 500. Where an exemplary embodiment of method 100 is implemented using software, the software may be stored in a computer program product and loaded into computer system 500 using removable storage drive 514, interface 520, and hard disk drive 512, or communications interface 524.

Embodiments of the present disclosure also may be directed to computer program products including software stored on any computer useable medium. Such software, when executed in one or more data processing device, causes a data processing device to operate as described herein. An embodiment of the present disclosure may employ any computer useable or readable medium. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, and optical storage devices, MEMS, nanotechnological storage device, etc.). The embodiments have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

While the foregoing has described what may be considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective spaces of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A method for controlling a laparoscopic instrument, the method comprising:
grasping a target utilizing the laparoscopic instrument by applying an initial trigger force to a trigger of the laparoscopic instrument;
obtaining an updated trigger force based on a first pinch force, a second pinch force, and a state of the laparoscopic instrument, the first pinch force applied to the target by an upper jaw of the laparoscopic instrument and the second pinch force applied to the target by a lower jaw of the laparoscopic instrument, the first pinch force equal to or larger than the second pinch force, obtaining the updated trigger force based on the first pinch force, the second pinch force,
and the state of the laparoscopic instrument comprising:
measuring, utilizing a force sensor, a pull force applied to the target responsive to applying the initial trigger force, the pull force comprising a magnitude and a direction,
the pull force associated with objects connected to the target;
extracting, utilizing one or more processors, a lower limit for the second pinch force and an upper limit for the first pinch force utilizing a three-zone grasp model associated with the magnitude of the pull force and the direction of the pull force;
setting, utilizing the one or more processors, a magnitude of the second pinch force equal to the lower limit;
calculating, utilizing the one or more processors, a magnitude of the first pinch force based on the second pinch force, the magnitude of the pull force, and the direction of the pull force;
generating, utilizing the one or more processors, a warning alarm responsive to the magnitude of the first pinch force equal to or larger than the upper limit;
calculating, utilizing the one or more processors, an average pinch force based on the first pinch force and the second pinch force responsive to the magnitude of the first pinch force smaller than the upper limit; and
calculating, utilizing the one or more processors, the updated trigger force based on an inverse force model associated with the average pinch force and the state of the laparoscopic instrument; and
grasping the target utilizing the laparoscopic instrument by applying the updated trigger force to the laparoscopic instrument.

2. The method of claim 1, wherein measuring the pull force comprises:
measuring the magnitude of the pull force; and
obtaining the direction of the pull force by measuring a pull force angle comprising an angle between a direction of the pull force and a bisector of a jaw angle, the jaw angle comprising an angle between a direction of the upper jaw and a direction of the lower jaw.

3. The method of claim 2, wherein extracting the lower limit and the upper limit comprises generating the three-zone grasp model associated with the direction of the pull force by:
generating a pinch-pull plane associated with the direction and the magnitude of the pull force,
generating the pinch-pull plane comprising:
a horizontal axis associated with a magnitude of the pull force; and
a vertical axis associated with a magnitude of the first pinch force and a magnitude of the second pinch force, the vertical axis perpendicular to the horizontal axis; and
dividing the pinch-pull plane into three separate zones comprising:
a slip zone limited to a slip curve;
a damage zone limited to a damage curve; and
a safe zone limited to the slip curve and the damage curve, the safe zone associated with the lower limit and the upper limit.

4. The method of claim 3, wherein dividing the pinch-pull plane into the three separate zones comprises deriving the slip curve, comprising:
replacing the target with a test object;
sequentially setting a magnitude of the second pinch force to a plurality of pinch force levels in an ascending order, a first pinch force level of the plurality of pinch force levels equal to zero;
obtaining a respective slip threshold of a plurality of slip thresholds for each of the plurality of pinch force levels by:
setting the magnitude of the pull force to zero;
increasing the magnitude of the pull force until the test object is slipped from the laparoscopic instrument; and
obtaining the respective slip threshold by measuring the magnitude of the pull force responsive to the test object being slipped; and
obtaining the slip curve by fitting a curve to variations of the plurality of slip thresholds with respect to variations of the plurality of pinch force levels, the slip curve associated with a specific direction of the pull force.

5. The method of claim 4, wherein dividing the pinch-pull plane into the three separate zones further comprises deriving the damage curve, comprising:
sequentially setting the magnitude of the pull force to a plurality of pull force levels in an ascending order, a first pull force level of the plurality of pull force levels equal to zero;
obtaining a respective damage threshold of a plurality of damage thresholds for each of the plurality of pull force levels by:
setting the magnitude of the first pinch force to zero;
increasing the magnitude of the first pinch force until a damaged area is generated on the test object; and obtaining the respective damage threshold by measuring the magnitude of the first pinch force responsive to the damaged area being generated; and obtaining the damage curve by fitting a curve to variations of the plurality of damage thresholds with respect to variations of the plurality of pull force levels, the damage curve associated with the specific direction of the pull force.

6. The method of claim 1, wherein calculating the magnitude of the first pinch force based on the second pinch force and the pull force comprises solving a static rotational equilibrium equation defined by the following:

$$F_{g1} - F_{g2} = F'_{pull}$$

where:

$F_{g1}$ is a magnitude of the first pinch force,
$F_{g2}$ is a magnitude of the second pinch force, and
$F'_{pull}$ is the magnitude of the pull force along an axis perpendicular to the bisector of the jaw angle.

7. The method of claim 1, wherein calculating the average pinch force based on the first pinch force and the second pinch force comprises averaging the magnitude of the first pinch force and the magnitude of the second pinch force.

8. The method of claim 1, wherein calculating the updated trigger force comprises:

obtaining the state of the laparoscopic instrument by:
measuring a jaw angle comprising an angle between a direction of the upper jaw and a direction of the lower jaw; and
measuring a wrist angle comprising an angle between a direction of a rod of the laparoscopic instrument and a bisector of the jaw angle, the wrist angle defined by the following:

$$\varphi = \cos^{-1}(|\cos \psi| \times |\cos \alpha|)$$

where:

$\varphi$ is the wrist angle,
$\psi$ is an amount of rotation of the laparoscopic instrument around a Y axis, and
$\alpha$ is an amount of rotation of the laparoscopic instrument around a Z axis; and calculating the updated trigger force according to an operation defined by the following:

$$F_t = g^*(F_g, \theta, \varphi)$$

where:
$F_g$ is the average pinch force magnitude,
$F_t$ is the updated trigger force magnitude,
$\theta$ is the jaw angle,
$\varphi$ is the wrist angle, and
$g^*(\cdot,\cdot,\cdot)$ is the inverse of the instrument force model of the laparoscopic instrument.

9. The method of claim 8, wherein calculating the updated trigger force further comprises:

pivotally connecting the upper jaw and the lower jaw by a pivot;

applying the initial trigger force to the laparoscopic instrument by exerting the initial trigger force to an actuation cable associated with the laparoscopic instrument;

grasping the target at a contact point of the target by applying the initial trigger force to the laparoscopic instrument; and obtaining the inverse force model according to a set of equations of the instrument force model defined by the following:

$$|\vec{F}_g| = \frac{(|\vec{F}_t| - f_{k0}) \times 0.5}{e^{\varphi(\mu')}} \times \frac{\left[\left(\frac{L}{\sin(0.5\theta + \alpha_0)} \times \cos(0.5\theta + \alpha_0)\right) - \mu(L+r)\right]}{d \times (\sin(0.5\theta + \alpha_0) + \mu\cos(0.5\theta + \alpha_0))}$$

$$\theta = 2 \times \sin^{-1}\left(\frac{L}{D - \left(x_{cable} - \frac{|\vec{F}_t|}{K_{inst}}\right)} - \alpha_0\right)$$

$$\mu' = 0.5\mu_1 + \mu_2$$

where:

$|\vec{F}_g|$ is a magnitude of the average pinch force,
$|\vec{F}_t|$ is a magnitude of the updated trigger force,
$f_{k0}$ is a static friction of the laparoscopic instrument,
$L$, $\alpha_0$, and $D$ are geometrical parameters of the laparoscopic instrument,
$\mu$ is a friction coefficient between a pin of the laparoscopic instrument and a cam slot of the lower jaw and the upper jaw,
$r$ is a radius of the pin,
$d$ is a distance between the pivot and the contact point,
$K_{inst}$ is a stiffness of the laparoscopic instrument,
$\mu_1$ is a friction coefficient between the actuation cable and an inner side of the instrument rod, and
$\mu_2$ is a friction coefficient between the actuation cable and an inner side of the instrument wrist.

* * * * *